US010226279B2

(12) United States Patent
Keady et al.

(10) Patent No.: US 10,226,279 B2
(45) Date of Patent: Mar. 12, 2019

(54) ENDOSCOPIC NEEDLE STYLET WITH ENHANCED-FLEXIBILITY LENGTHS

(71) Applicant: Cook Medical Technologies LLC, Bloomington, IN (US)

(72) Inventors: Fionán Keady, County Galway (IE); John Neilan, County Galway (IE); James Butler, County Tipperary (IE); Shay Joseph Lavelle, County Limerick (IE)

(73) Assignee: Cook Medical Technologies LLC, Bloomington, IN (US)

( * ) Notice: Subject to any disclaimer, the term of this patent is extended or adjusted under 35 U.S.C. 154(b) by 301 days.

(21) Appl. No.: 15/146,178

(22) Filed: May 4, 2016

(65) Prior Publication Data
US 2016/0331405 A1    Nov. 17, 2016

Related U.S. Application Data

(60) Provisional application No. 62/161,577, filed on May 14, 2015.

(51) Int. Cl.
A61B 17/34 (2006.01)
A61B 8/12 (2006.01)
(Continued)

(52) U.S. Cl.
CPC ............ *A61B 17/3478* (2013.01); *A61B 8/12* (2013.01); *A61B 10/04* (2013.01);
(Continued)

(58) Field of Classification Search
CPC ................ A61B 10/04; A61B 17/3478; A61B 2010/045; A61B 2017/00867; A61B 2017/3413; A61B 8/12
See application file for complete search history.

(56) References Cited

U.S. PATENT DOCUMENTS 3,558,369 A    1/1971    Wang et al.
4,068,659 A    1/1978    Moorehead
(Continued)

FOREIGN PATENT DOCUMENTS

EP    0 928 605 A2    7/1999
EP    0 806 220 B1    11/2003

OTHER PUBLICATIONS

Cook Medical Instruction manual No. IFU0077-3, titled "EchoTip ProCore® HD Ultrasound Biopsy Needle", 88 pgs.
(Continued)

*Primary Examiner* — Jocelin Tanner
(74) *Attorney, Agent, or Firm* — Brinks Gilson & Lione

(57) ABSTRACT

A single-wire stylet may be constructed as an elongate single-wire, memory-metal alloy body with a generally cylindrical body profile, extending distally from a proximal end terminus, where embodiments include a polymeric distal tip member fixedly attached directly at a distal end of the single-wire body. At least one lengthwise portion of the single-wire body is at least partially in martensitic phase at operating temperatures at and below about 37° C. Where present, the polymeric distal tip member has a generally cylindrical body profile circumferentially bounded by an outer circumference substantially equal to or greater than that of the metal body. The polymeric distal tip member may be overmolded upon a distal-end tip length of an elongate single-wire, memory-metal alloy stylet body, where the distal end and/or discrete intermediate distal-portion length (s) that include martensitic-phase alloy and any polymeric member have greater flexibility than a proximal-most length of the alloy stylet body.

16 Claims, 5 Drawing Sheets

(51) Int. Cl.
*A61B 10/04* (2006.01)
*A61B 17/00* (2006.01)
(52) U.S. Cl.
CPC .............. *A61B 2010/045* (2013.01); *A61B 2017/00867* (2013.01); *A61B 2017/3413* (2013.01)

(56) References Cited

U.S. PATENT DOCUMENTS

| | | | |
|---|---|---|---|
| 4,068,660 A | 1/1978 | Beck | |
| 5,171,383 A | 12/1992 | Sagaye et al. | |
| 5,514,115 A | 5/1996 | Frantzen et al. | |
| 5,624,508 A | 4/1997 | Flomenblit et al. | |
| 5,766,218 A | 6/1998 | Arnott | |
| 6,149,742 A | 11/2000 | Carpenter et al. | |
| 6,231,564 B1 | 5/2001 | Gambale | |
| 6,485,507 B1 | 11/2002 | Walak et al. | |
| 7,670,302 B2 * | 3/2010 | Griffin | A61L 31/022 600/585 |
| 8,128,579 B2 | 3/2012 | Chen et al. | |
| 8,414,571 B2 | 4/2013 | Pellegrino et al. | |
| 2003/0233025 A1 * | 12/2003 | Saadat | A61B 1/0008 600/114 |
| 2005/0115624 A1 | 6/2005 | Walak | |
| 2007/0135734 A1 | 6/2007 | Reynolds et al. | |
| 2010/0159117 A1 | 6/2010 | Griffin et al. | |
| 2010/0160731 A1 | 6/2010 | Gionvannini et al. | |
| 2011/0009878 A1 * | 1/2011 | Haldeman | A61N 1/056 606/129 |
| 2011/0071429 A1 | 3/2011 | Weisman | |
| 2012/0245486 A1 * | 9/2012 | Melchiorri | A61B 10/0275 600/567 |
| 2014/0114255 A1 * | 4/2014 | Irwin | A61M 25/0102 604/164.06 |
| 2014/0276224 A1 | 9/2014 | Ranganathan et al. | |
| 2016/0038126 A1 * | 2/2016 | Brooks | A61B 10/0275 600/427 |

OTHER PUBLICATIONS

Cook Medical Instruction manual No. IFU0101-0, titled "EchoTip® Ultra Ultrasound Needle", 48 pgs.
International Search Report and Written Opinion for corresponding application No. PCT/US2016/030541, 12 pgs.

* cited by examiner

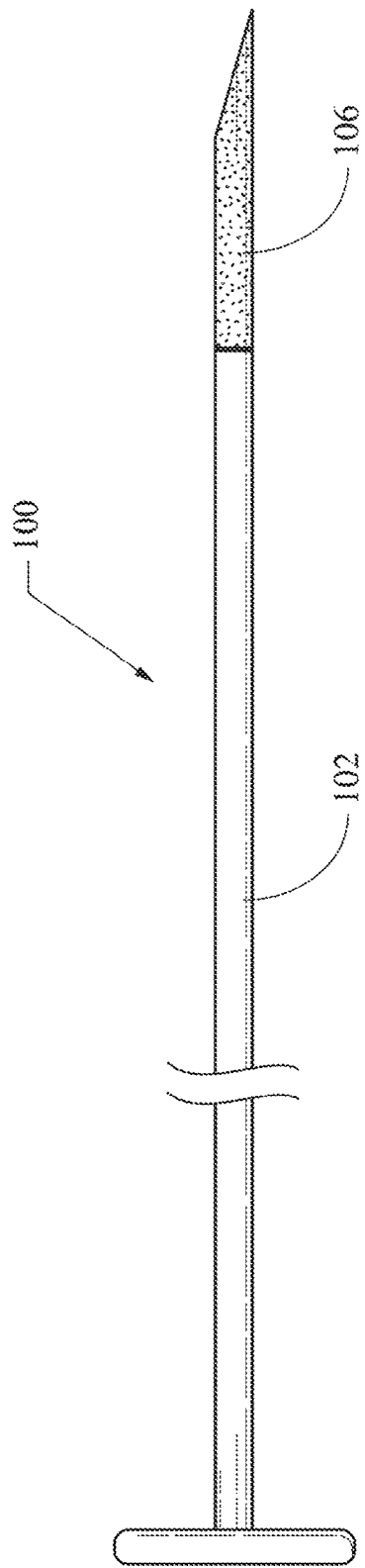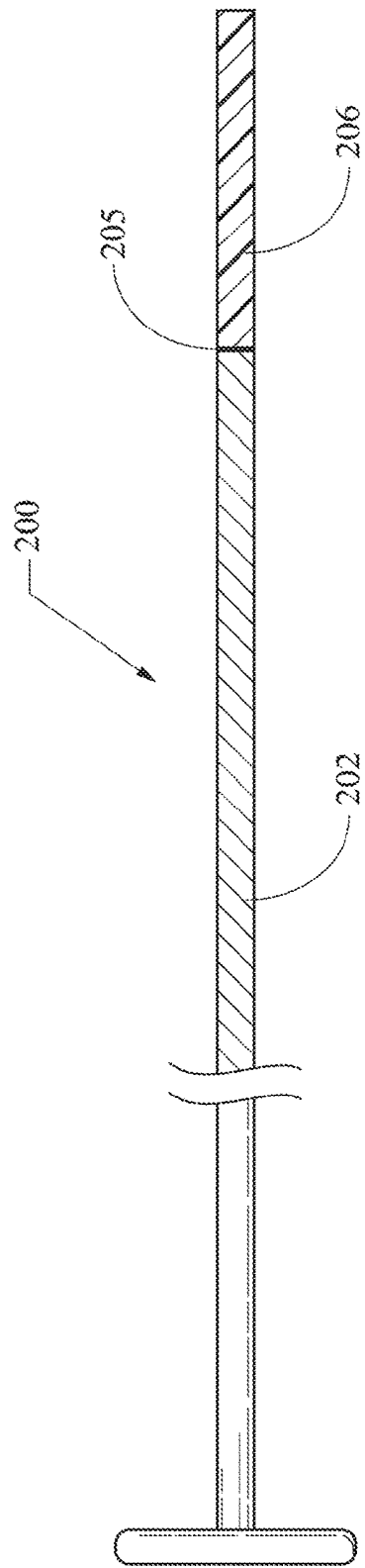

ENDOSCOPIC NEEDLE STYLET WITH ENHANCED-FLEXIBILITY LENGTHS

CROSS-REFERENCE TO RELATED APPLICATIONS

This application is a non-provisional application which claims priority to U.S. provisional application Ser. No. 62/161,577, filed May 14, 2015, which is incorporated by reference herein in its entirety.

TECHNICAL FIELD

Embodiments disclosed herein generally relate to medical device appliances. More particularly embodiments disclosed herein relate to stylets used within the lumen of endoscopic ultrasound needles during endoscopic ultrasound (EUS) procedures.

BACKGROUND

Endoscopic ultrasound (EUS) procedures including endobronchial ultrasound (EBUS) procedures, as well as other endoscopy procedures (e.g., endoscopic retrograde cholangiopancreatography (ERCP) techniques used for viewing and treating the ducts that drain the liver and pancreas) provide advantageous, minimally-invasive means for diagnosis and treatment of many conditions. The body structures and passages that must be navigated with the scope-based devices present challenges for minimizing procedure times while maximizing efficacy of diagnostic and/or therapeutic procedures.

For example, with reference to gastrointestinal procedures, biliary ducts form a drainage routes into the duodenum from the liver and gallbladder and they join the pancreatic duct, just before they drain into the duodenum about 3 inches from the stomach. The drainage opening is called the papilla (Ampulla of Vater). The papilla is surrounded by a circular muscle, called the sphincter of Oddi. During ERCP, X-ray contrast dye may be injected into the bile duct, the pancreatic duct, or both via a catheter disposed through a working channel of an endoscope to aid fluoroscopic visualization of procedures. Those same systems may be accessed and visualized using EUS procedures, where use of ultrasound helps to reduce the amount of fluoroscopy exposure time spent by a patient and treating personnel.

A broad variety of techniques using ERCP and EUS (including in the gastrointestinal tract and elsewhere in patient bodies) have been and continue to be developed for minimally-invasive diagnosis and treatment of various conditions in a patient's gastrointestinal tract, and particularly in the structures of the biliary and pancreatic systems branching off from the duodenum. For a number of procedures using small gauge needles (often 19 ga. or smaller), the needle is introduced with a stylet disposed through the entire length or nearly the entire length of its longitudinal needle lumen. A standard bevel-tipped stylet 174 is shown in FIG. 1, including a proximal end cap 176 and a flexible elongate body 178. The stylet provides columnar strength while the needle is being directed to a target site, as well as minimizing the likelihood that an open distal tip and/or side aperture of, for example, a biopsy needle will collect tissue en route to the actual site being targeted.

In a biopsy procedure, the stylet will be removed from (or at least partially longitudinally retracted within) the needle lumen, typically after the needle is directed through an endoscope working channel so that its distal end is in or near the target site. As shown in FIG. 2, the endoscope (illustrated here as a duodenoscope 181, but readily understandable with application to an EUS scope) is directed down a patient's esophagus 191, then through the body, and up and around the pylorus of the stomach 193, then down/around into the duodenum 195. For the side-viewing camera and ports to properly orient relative to the sphincter of Oddi 197 and access the primary and branching ducts/passages of the biliary tree 199, the distal end portion of the endoscope 181 may be flexed/bent 90 degrees or more relative to longitudinal axis of the scope and to the already-curved scope body portion situated through the pylorus and duodenum, which is also shown. As such, the coaxial arrangement of a stylet within a biopsy needle assembly, oriented through an endoscope working channel is placed through a series of curves and turns between the proximal end accessed by an endoscopist and other treating personnel and the distal end (e.g., accessing the biliary tree), along and through all three axes of the patient's body.

It will be appreciated that this presents a relatively tortuous path for a needle disposed through the length of the endoscope 181. The same would be true for an EUS procedure, whether access is gained through a cannulated sphincter or by traversing a wall of the stomach, duodenum, or other structure. Thus, a stylet occupying the needle lumen may require significant force for withdrawal and removal (e.g., about 50 to about 100 Newtons), due to the binding friction between the outer surface of the stylet and the inner needle lumen surface along their respective lengths—and particularly along lengths where the scope is twisted and/or tightly curved. Stated differently, those of skill in the art will appreciate that certain points or lengths along the path of a stylet through a needle lumen may present greater frictional contact/binding force due to curvature of the needle (both on its own and relative to/interacting with an accessory channel of an endoscope through which it is disposed), causing an increased removal force required to remove the stylet from the needle lumen, as compared to a less curved, twisted, or otherwise distorted path. This higher level of removal force is inconvenient to the users, and it may have a negative impact on efficient workflow (e.g., by increasing the likelihood that the needle and/or scope is moved out of the desired position and/or orientation during stylet removal, by increasing procedure time, or other factors).

It may be desirable to provide a stylet and a stylet-needle system including a stylet structure that provides for reduced removal force without diminishing its other stylet functionality.

BRIEF SUMMARY

In one aspect, embodiments disclosed herein include a single-wire stylet including a proximal end terminus and a distal end terminus, constructed as an elongate single-wire, memory-metal alloy body with a generally cylindrical body profile that is circumferentially bounded by a first outer circumference, extending distally from the proximal end terminus, where embodiments include a polymeric distal tip member fixedly attached directly at a distal end of the single-wire body. At least a lengthwise portion of the single-wire body is at least partially in martensitic phase at operating temperatures at and below about 37° C. Where present, the polymeric distal tip member has a generally cylindrical body profile circumferentially bounded by a second outer circumference that is substantially equal to or greater than the first outer circumference.

In one aspect, stylet embodiments disclosed herein may include a polymeric distal tip member overmolded upon a distal-end tip length of an elongate single-wire, memory-metal alloy stylet body, where the distal end and/or discrete intermediate distal portion length(s) have greater flexibility than a proximal-most length of the stylet.

BRIEF DESCRIPTION OF THE DRAWINGS

FIGS. 3A-3C show stylet embodiments with a generally consistent outer circumference along the stylet body length.

DETAILED DESCRIPTION

Figure 1:
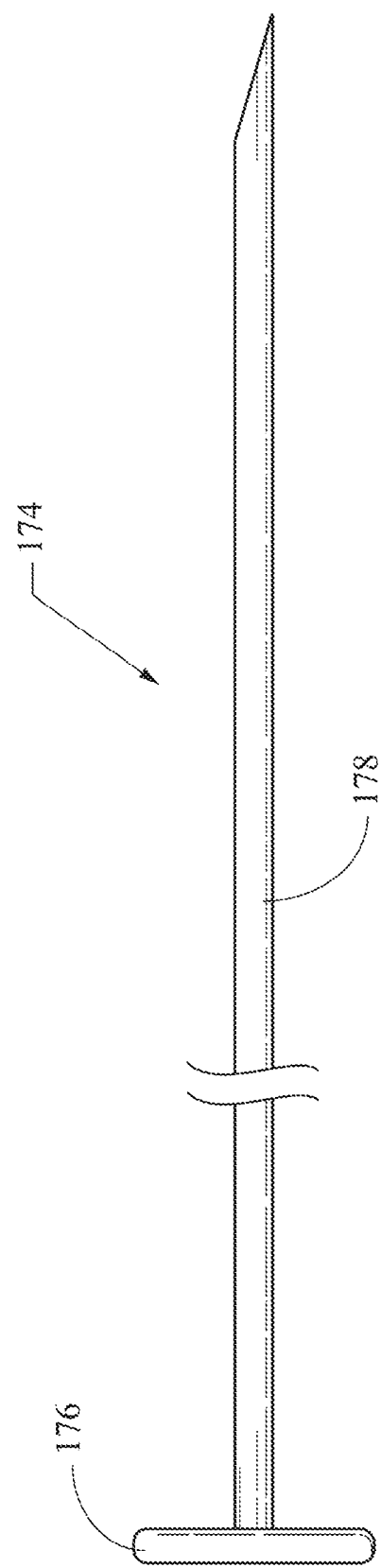
FIG. 1 shows a standard prior art stylet.

Various embodiments are described below with reference to the drawings in which like elements generally are referred to by like numerals. The relationship and functioning of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments disclosed herein, such as—for example—conventional fabrication and assembly, as well as showing highly flexible structures (e.g., stylets and/or needles) only in a generally straight line, when those of skill in the art will appreciate that they can be highly flexible for navigation through tortuous passages.

A stylet for within an endoscopy needle is described, including features that provide reduced removal force as compared to a standard stainless steel, nitinol, or other standard stylet. The phrase "within an endoscopy/endoscopic needle" should be understood as meaning that all or substantially all of the stylet length fits within and, when in use will, at some time, be disposed within the lumen of a needle, including that the distal end terminus of the stylet will not extend beyond the distal needle end terminus. The phrase "substantially within an endoscopy/endoscopic needle" should be understood as meaning that substantially all of the stylet length fits within and, when in use will, at some time, be disposed within the lumen of a needle, including that the distal end terminus of the stylet will not extend substantially beyond the distal needle end terminus (e.g., in certain embodiments, a stylet may extend up to a few—that is most likely fewer than about 10, and highly likely fewer than 5—millimeters beyond a surrounding needle's distal end terminus). The reduced removal force may be provided by enhanced flexibility along at least a length of a metallic stylet body portion (e.g., by constructing it of a memory metal material that maintains some or all martensitic phase at operating temperatures between about 20° C. to about 40° C., and at least at or below the operating temperature of a patient's body such as 37° C.) and providing a more flexible, lower friction polymeric distal tip member along or defining a distalmost length of the stylet body, as is described below.

Methods of making a stylet may include specific heat-treatment of one or more lengths of a memory metal wire (e.g., a nickel titanium or other memory metal alloy) to provide desired flexibility. In particular, it is desirable that up to about 30% of the distal length of a stylet be highly flexible so as to minimize retraction force. In some embodiments, up to 70%, or even up to 100% of the stylet body length may be configured for increased flexibility (i.e., as compared to a standard metal alloy needle stylet of the same length and configured for use within the same needle gauge). A method has been devised to fabricate a hybrid stylet comprising a memory metal alloy that can exhibit two different flexibility behaviors at temperature ranges including body temperature (37° C.). The technology devised enables the creation of a single-wire stylet, the metallic length of which is free from any joints or welds. The hybrid stylet, which may be made from a single continuous wire, can be used for endoscopic and other applications where a needle (e.g., a biopsy needle or access needle) occupied by the stylet may provide points and/or lengths of constriction that increase retraction force.

The method includes controlling the austenite transformation temperatures ($A_s$, $A_f$=austenite start, austenite finish temperatures) of a shape memory alloy such as Nitinol in different portions of a stylet. When $A_s$ and $A_f$ have values below body temperature, the shape memory alloy is fully austenitic at body temperature and superelastic deployment of a pre-formed shape is possible. However, when $A_s$ and $A_f$ have values above body temperature, the memory metal alloy remains martensitic at body temperature and plastic deformation remains readily usable/available, which provides for the desired flexibility or malleability of the present stylet design. As such, at least a lengthwise portion of the single-wire body of stylet embodiments described herein preferably remains in martensitic phase at operating temperatures between about 20° C. to about 40° C., and most preferably remains in martensitic phase at operating temperatures of body temperature plus the standard variations of temperature likely in an operating environment (e.g., for a human patient, about 37° C., plus up to about 10° C.). Those of skill in the art will appreciate that lower operating temperatures are unlikely to effect a phase change that would decrease flexibility of a martensitic shape memory wire length.

The invention is defined by the claims, may be embodied in many different forms, and should not be construed as limited to the embodiments set forth herein; rather, these embodiments are provided so that this disclosure will be thorough and complete, and will fully convey enabling disclosure to those skilled in the art. As used in this specification and the claims, the singular forms "a," "an," and "the" include plural referents unless the context clearly dictates otherwise.

The terms "proximal" and "distal" are used and defined herein in the common usage sense where they refer respectively to a handle/doctor-end of a device or related object and a tool/patient-end of a device or related object. The term "stylet" as used herein is should be understood as different that guidewire structures that are used through, and extending well beyond the distal end of, endoscopic and other minimally-invasive needles, where a stylet of the present disclosure is a single-wire device that expressly excludes an overlying coil wire, and that does not include other distal tip features configured for steerability in the manner of guidewires. The term "about" when used with reference to any dimension, proportion, or other quantitative value is intended to communicate a definite and identifiable value within the standard parameters that would be understood by one of skill in the art (a medical device engineer with significant experience in the field of minimally invasive endoscopy needles and devices), and should be interpreted to include at least any legal equivalents, minor but functionally-insignificant variants, and including at least mathematically significant figures. The relative definitions of flexibility (e.g., "more flexible" and "less flexible" with reference to a stylet) will readily be understood by those of skill in the art as used herein; specifically, a "more flexible" length will be coilable and bendable around smaller/tighter radii of curvature than will a "less flexible" length—without imposing a crimp, bend, fold or other permanent distortion.

One embodiment of a stylet for use within an endoscopy needle is described with reference to FIG. 3A, which shows a simplified/diagrammatic side view of a first stylet embodiment 100. The stylet 100 includes an elongate single-wire, memory-metal alloy body 102 with a generally cylindrical body profile that is circumferentially bounded by a first outer circumference. For example, the transverse cross-section of the body 102 may be circular or at least generally circular (that is, allowing for manufacturing tolerances and including near-circular geometric shapes). A polymeric distal tip member 106 is fixedly attached directly at a distal end of the single-wire body 102. The polymeric distal tip member 106 has the same generally cylindrical body profile as the single-wire body 102, and it is circumferentially bounded by a second outer circumference that is equal or substantially equal to the first outer circumference. By "substantially equal," those of skill in the art will understand that the outer circumferences are generally the same within normal manufacturing tolerances and variances due to slight relative contraction or expansion upon heating, cooling, and during use. The polymeric distal tip member 106 is shown with a beveled distal terminal end tip.

The polymeric distal tip member of this and other embodiments may include or consist of any biocompatible polymer suitable for forming into the structure described. In certain embodiments, the polymeric distal tip member may be constructed of a polymer selected from a polyetheretherketone (PEEK), polycarbonate, polytetrafluoroethylene (PTFE), silicone, latex rubber, non-latex rubber, thermoplastic polymers (including, e.g., PEBAX), and any combination thereof. The external surface of the polymeric distal tip member preferably is lubricious or otherwise configured to present a low efficient of friction when used in the lumen of a needle (where the inner circumference of the needle is about the same as or only slightly greater than the outer circumference of the polymeric distal tip member, as is well-known and characterized for relative proportions of stylets and coaxially-overlying needles). The fixed attachment of the polymeric distal tip member to the single-wire body may be effected by one or more of overmolding, adhesive, epoxy, friction-fit interface, or any combination thereof, as well as other means known or developed in the art for attaching the particular selected construction materials.

Different stylet embodiments may have different lengths. For example, a stylet configured for use in an endobronchial ultrasound needle may be about 1 meter in length, while a stylet configured for use in a gastrointestinal endoscopic ultrasound needle (e.g., for accessing and biopsying the head of a human pancreas may be about 1.7 meters in length. Preferably, at least about one-tenth, and more preferably at least about one-fourth of the distal length to about one-half of the distal length of the single-wire metal alloy body is in martensitic phase at operating temperatures (e.g., patient body temperature for a human or non-human patient). For a stylet single-wire body in which less than the entire length is in martensitic phase at operating temperatures, the other (non-martensitic phase length) may undergo a thermal process different than the distal martensitic phase length, as set forth below.

To fabricate a hybrid stylet single-wire body that has a distal lengthwise portion with different martensitic/austenitic state properties that a proximal lengthwise portion of the wire, the different portions will undergo different thermal processing treatments. As a result, different austenite transformation temperatures are achieved in each portion of the wire. The specific heating time and temperature for each length will be determined by the specific memory metal alloy selected, as is known in the art. Typically, heat setting is carried out at a temperature between about 350° C. and about 550° C. for a time duration of about 5-180 min. For the present embodiments, the length of single-wire body that is to remain in a martensitic phase at operating temperature within a patient body, the time and temperature of heat-treatment are likely to be near the upper ends of those ranges, depending upon the specific memory metal alloy selected. Most preferably both the austenite start ($A_s$) and the austenite finish ($A_f$) temperatures will be above the operating temperature within a patient body, e.g., greater than about 37° C., where certain embodiments preferably will maintain the desired lengthwise portion of the single-wire body in martensitic phase at operating temperatures up to about 40° C. or greater. The heat treatment may be isolated to a desired length of a continuous piece of wire using means known in the art, including passing current along the wire between selected contact points defining the length being treated. The non-heat-treated proximal length, if any, may be protected from transformation by means known in the art (e.g., exposure to cooling fluid during the heat treatment of the other length(s)).

Depending upon the specific memory metal alloy selected, the wire as drawn may have desirable flexibility/malleability properties for a proximal length. As such, the proximal length may be treated in a manner providing $A_s$ and/or $A_f$ temperatures that are at or below the aforementioned operating temperatures. In this manner, the proximal length may be more rigid than the treated/martensitic phase distal length (although still retaining desirable flexibility for use in the manner of known stylets). The change in the austenite transformation temperatures in the distal portion of the single-wire body as a consequence of the heating (e.g., in a sand bath, by use of current, or other means) may be understood in view of microstructural changes that occur. For example, when the shape memory alloy is an equiatomic or near-equiatomic nickel-titanium (Ni—Ti) alloy, the temperature increase may cause nickel-rich precipitates to form in the alloy, producing localized shifts in composition and depleting the Ni—Ti alloy matrix of nickel.

However, the overall composition of the alloy remains the same. Due to the localized depletion of nickel from the Ni—Ti alloy matrix, the austenite transformation temperatures ($A_s$ and $A_f$) may increase. When heated for sufficient time, the $A_s$ temperature of the distal portion of the single-wire body increases above 37° C., ensuring that the Ni—Ti alloy remains martensitic at body temperature. Thus, the distal portion of the stylet body most likely to encounter binding, constriction, and/or tortuous passages that would increase retraction force. Because only the distal portion of the single-wire stylet body experiences the heat treatment (e.g., due to the selected method of heating, optionally complemented by cooling of the proximal portion), the initial austenite transformation temperatures in the proximal portion do not change substantially. Accordingly, the proximal portion of the stylet remains flexible and may be superelastic at body temperature. The foregoing methods may be used in preparing the single-wire body for each of the embodiments described herein.

It should also be appreciated that this disclosure provides for a stylet embodiment not including a polymer distal tip member, but just a single-wire body. In such an embodiment, a distalmost length of the wire is malleable and more highly flexible than a proximal-most length, because the distalmost length is prepared and maintained in at least a partially martensitic phase up to and/or above a patient's body temperature (e.g., 37° C., and as described elsewhere herein), providing for the desirable performance features described with reference to the other embodiments of this disclosure. Such an embodiment may have a general external appearance similar or even identical to the stylet of FIG. 1, but will have the novel flexibility differences based upon the martensitic properties of selected and identified length(s) of the single-wire body.

Another embodiment of a stylet for use within an endoscopy needle is described with reference to FIG. 3B, which shows a simplified/diagrammatic partial-longitudinal-section view of a second stylet embodiment 200. The stylet 200 includes an elongate single-wire, memory-metal alloy body 202 with a generally cylindrical body profile that is circumferentially bounded by a first outer circumference. For example, the transverse cross-section of the body 202 may be circular or at least generally circular, although non-circular transverse section bodies may be considered as cylindrical within the scope of the present application. A polymeric distal tip member 206 is fixedly attached directly at a distal end of the single-wire body 202. The polymeric distal tip member 206 has the same generally cylindrical body profile as the single-wire body 202, and it is circumferentially bounded by a second outer circumference that is equal or substantially equal to the first outer circumference. The joint 205 of the polymeric distal tip member 206 with the single-wire body 202 may be secured by epoxy, adhesive, or any other appropriate means known or developed in the art. The distal end terminus of the polymeric distal tip member 206 is shown as having a blunt flat end, although this embodiment and all others may have any number of end-terminal shapes, including by way of non-limiting example, hemispherical or otherwise rounded, flat, beveled, conical, or otherwise singly or multiply pointed, or convex.

Another embodiment of a stylet for use within an endoscopy needle is described with reference to FIG. 3C, which shows a simplified/diagrammatic longitudinal section view of a third stylet embodiment 300. The stylet 300 includes an elongate single-wire, memory-metal alloy body 302 with a generally cylindrical body profile that is circumferentially bounded by a first outer circumference. A polymeric distal tip member 306 is fixedly and directly attached by being overmolded (or otherwise permanently/fixedly attached) around a distalmost end length 304 of the single-wire body 302. The polymeric distal tip member 306 has the same generally cylindrical body profile as the single-wire body 302, and it is circumferentially bounded by a second outer circumference that is equal or substantially equal to the first outer circumference.

Most of the distalmost end length 304 has a third outer circumference less than the first and second outer circumferences, and it is shown with an enlarged portion 304a that may help secure the polymeric distal tip member 306 alone or along with other fastening means (such as, for example, epoxy, adhesive, etc.). The enlarged portion 304a is shown as having frustoconical geometry, but those of skill in the art will appreciate that other shapes can be provided to assist inter-engagement of the distalmost end length 304 with the polymeric distal tip member 306. In other embodiments (not shown), the distalmost end length 304 may be tapered, include a wavy, crenellated, serrated, or other surface geometry that provides at least lengthwise portion including the third outer circumference less than the first and second outer circumferences. The distalmost end length 304 of the single-wire body 302 preferably occupies one-half or less of the longitudinal length of the polymeric distal tip member 306. For example, in this and other embodiments a third outer circumference may be about 65% to about 95% of the second outer circumference. As such, the unoccupied distalmost length of the polymeric distal tip member 306 preferably will be even more flexible than the martensitic phase contacting/immediately-adjacent length of the single-wire body 302, which will further provide for decreasing likelihood of binding/increased retraction force attributable to stylet stiffness through certain lengths of a needle lumen (or other lumen) during use.

Figure 3C:
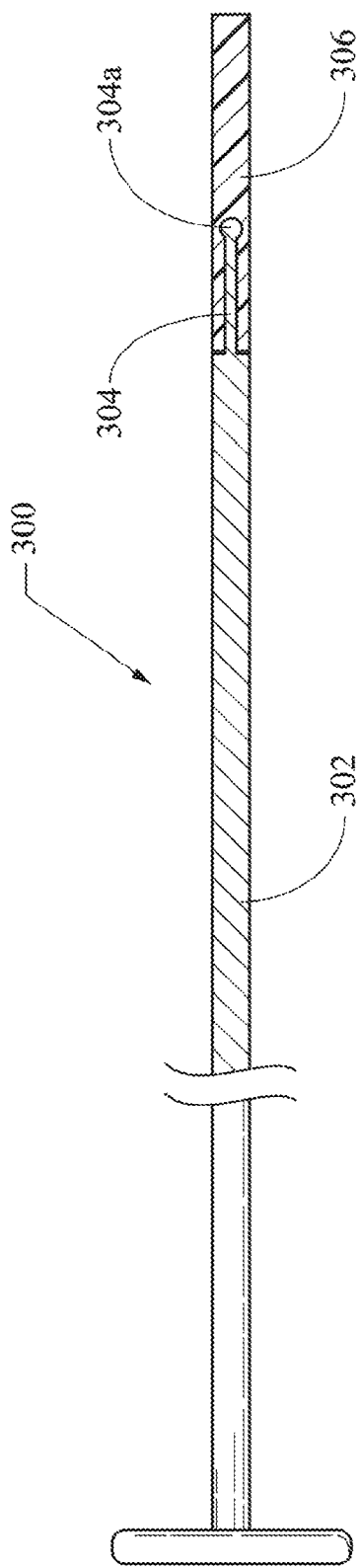

For each of the embodiments of FIGS. 3A-3C, the first and second outer circumference will be approximately the same as or only slightly less than the inner circumference of a needle in and through which each stylet embodiment will operate and be disposed.

As such, for use in a needle system, the absolute dimensions of the stylet body with its polymeric distal tip member will be determined by the needle selected. For example, a 19-gauge needle including a central longitudinal needle lumen that is 170 cm long preferably will receive and contain for use during endoscopic introduction a stylet embodiment having an outer circumference about the same as or only very slightly less than the inner needle circumference (understood by those of skill in the art to have about the same respective outer diameter and inner diameter for a needle and stylet with circular transverse cross-sections). The combined length of the single-wire body and its polymeric distal tip member for such a needle will be about 170 cm. The polymeric distal tip member may comprise at least about 5% of the total stylet length, and in some bodies may comprise up to about 10%, about 15%, or even about 20% thereof. The distal portion of the needle comprising the enhanced flexibility of the martensitic portion of memory metal single-wire body and polymeric distal tip member most preferably includes sufficient length to account for the length of the stylet that is most likely to encounter the constricted path and/or binding regions or points when deployed within a needle through an accessory/working channel of an endoscope. In the case of a gastrointestinal endoscope, a distal length of these more-flexible portions may include up to about one-half of the stylet length. In most embodiments, at least about one-tenth up to about one-third of the stylet's distalmost length will account for those regions where the enhanced flexibility will provide advantage over prior art stylets.

In one example, a 19-gauge, 1.7 m biopsy needle is provided including a tissue-collection side aperture disposed within a distalmost 10-12 mm length of the needle body. A stylet according to any embodiment herein described (including variants that combine or exchange features of separately described embodiments) is provided through the needle lumen, occupying the entire length thereof without extending substantially past the distal terminal needle tip. The polymeric distal tip member occupies all or very nearly all the cross-sectional needle lumen area for at least the distalmost needle lumen length through and including the side aperture, such that the polymeric distal tip member completely covers/obscures the side aperture when the stylet is fully engaged into the needle lumen. The more-flexible stylet length including the martensitic phase-containing single-wire stylet body length extends along at least 15%-20% of the entire stylet body length, where the remaining proximal length may be in the form/phase as drawn or may be in an austenitic phase. One exemplary needle construction with which the present stylet embodiments may be useful is described in U.S. Pat. Publ. No. 2012/0253228 to Schembre, et al., which is incorporated herein by reference. It should also be appreciated that an intermediate and/or proximal length of a single-wire stylet body of the present disclosure (that is a length proximal of a "martensitic at/below body temperature" wire body length) may be configured with a shapeset memory promoting and/or imposing self-coiling behavior in the manner disclosed in U.S. Pat. App. Pub. No. 2014/0114254 to Irwin, et al., which is incorporated herein by reference.

In one example of an embodiment, a 22-gauge biopsy needle that is 1.7 m in length, may be provided for fine needle aspiration or fine needle biopsy (e.g., with a gastrointestinal EUS endoscope). A stylet according to any embodiment herein described (including variants that combine or exchange features of separately described embodiments) may be provided in and through the needle lumen, occupying the entire length thereof without extending substantially past the distal terminal needle tip. The metallic and/or polymeric distal tip member will occupy all or very nearly all the cross-sectional needle lumen area for at least the distalmost needle lumen length. The more-flexible stylet length including the polymeric tip and/or martensitic phase-containing single-wire stylet body length extends along at least 15%-20% of the entire stylet body length, where the remaining proximal length may be in the form/phase as drawn or may be in an austenitic phase. In another embodiment, a 22-gauge biopsy needle may be provided with a length appropriate for use in an endobronchial ultrasound (EBUS) endoscope, and—prospectively—with a different distal-end biopsy-collection structure than in the 1.7 m embodiment. Those of skill in the art will appreciate that many EUS and EBUS needles are generally the same in their design characteristics. The main differences are in the overall length and needle gauge (Needle OD), as well as the particular tip shape that may be chosen for biopsy or other purposes. As such, those skilled in the art will appreciate that additional examples of stylet embodiments of the present disclosure will be very similar in design to those expressly disclosed here and may be constructed as informed by the present disclosure without undue experimentation.

Figure 4A:
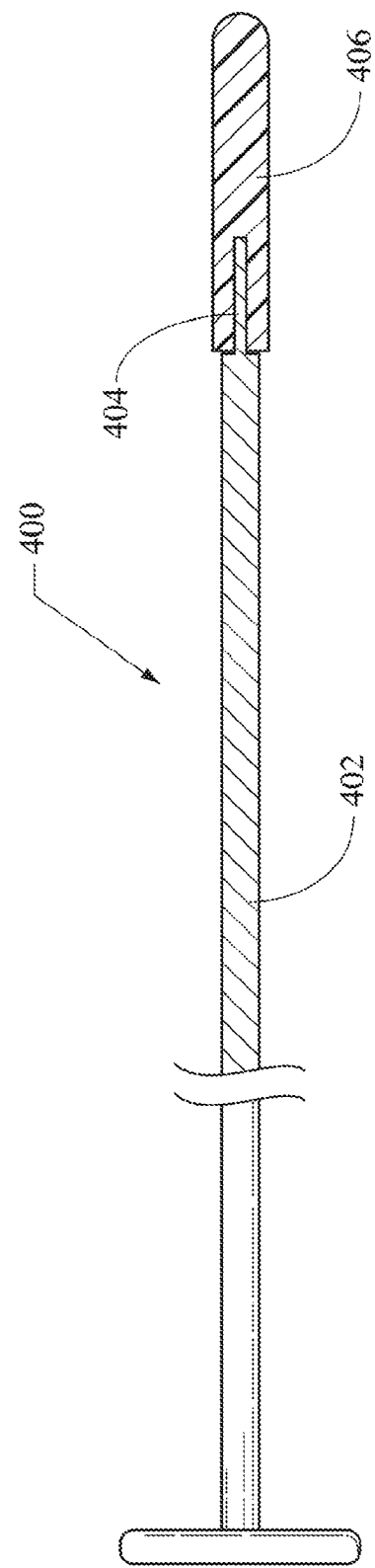
FIGS. 4A-4C show stylet embodiments with a generally consistent outer circumference along a metal stylet body length with a larger outer circumference along a distalmost polymeric tip body length.

Another embodiment of a stylet for use within an endoscopy needle is described with reference to FIG. 4A, which shows a simplified/diagrammatic longitudinal section view of a fourth stylet embodiment 400. The stylet 400 includes an elongate single-wire, memory-metal alloy body 402 with a generally cylindrical body profile that is circumferentially bounded by a first outer circumference. A polymeric distal tip member 406 is overmolded (or otherwise permanently/fixedly attached) around a distalmost end length 404 of the single-wire body 402. The polymeric distal tip member 406 has a generally cylindrical body profile like the single-wire body 402, and it is circumferentially bounded by a second outer circumference that is greater than the first outer circumference. For example, in this and other embodiments the first outer circumference may be about one-half to about 65% to about 95% of the second outer circumference.

Most of the distalmost end length 404 of the single-wire body 402 has a third outer circumference that is about the same as the first outer circumference (although it may be somewhat lesser or greater) and that is less than the second outer circumference. The distalmost end length 404 of the single-wire body 402 preferably occupies one-half or less of the longitudinal length of the polymeric distal tip member 406. As such, the unoccupied distal-most length of the polymeric distal tip member 406 preferably will be even more flexible than the martensitic phase contacting/immediately-adjacent length of the single-wire body 402, which will further provide for decreasing likelihood of binding/increased retraction force attributable to stylet stiffness through certain lengths of a needle lumen (or other lumen) during use.

Figure 4B:
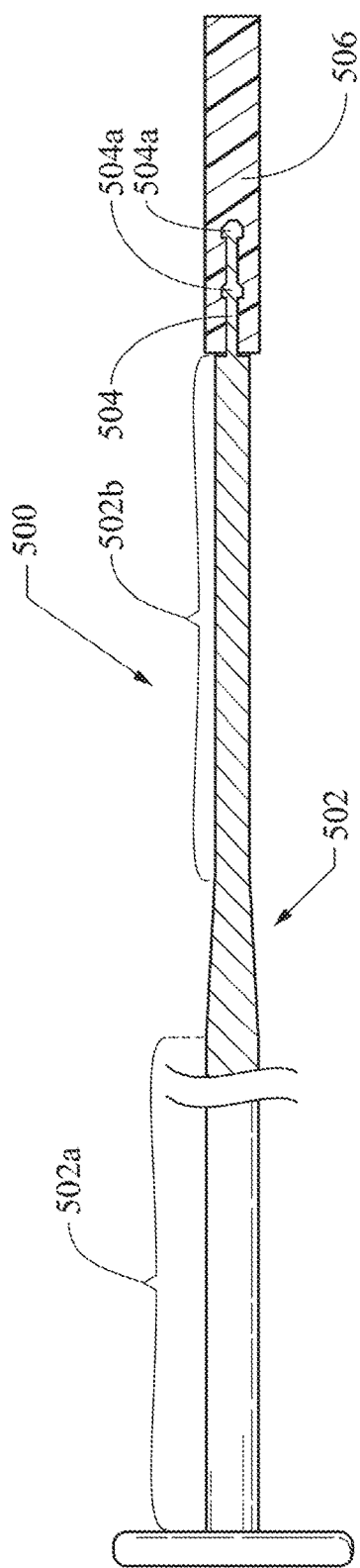

Another embodiment of a stylet for use within an endoscopy needle is described with reference to FIG. 4B, which shows a simplified/diagrammatic longitudinal section view of a fifth stylet embodiment 500. The stylet 500 includes an elongate single-wire, memory-metal alloy body 502 with a generally cylindrical body profile that is circumferentially bounded by a first outer circumference along a proximal-most longitudinal length 502a. A polymeric distal tip member 506 is overmolded (or otherwise permanently/fixedly attached) around a distalmost end length 504 of the single-wire body 502. The polymeric distal tip member 506 has a generally cylindrical body profile like the single-wire body 502, and it is circumferentially bounded by a second outer circumference that is greater than the first outer circumference.

Most of the distalmost end length 504 of the single-wire body 502 (disposed within the polymeric distal tip member) has a third outer circumference that is less than the first outer circumference and that is less than the second outer circumference. The outer circumference of the proximal-most longitudinal length 502a tapers to a fourth outer circumference along an intermediate longitudinal length 502b, which is less than the first outer circumference and which may be less than, the same as, or greater than the third outer circumference. The proximal length 502a including the first outer circumference will preferably provide desirable pushability and trackability along the proximal-most about 10% to about 70% of stylet body length, while the tapering length to the smaller fourth outer circumference preferably will provide a smooth transition that promotes responsiveness and is consistent with providing enhanced flexibility and/or reduced likelihood of binding or retraction force required for at least a distal stylet length portion. This may be referred to as "stylet removal force."

Figure 2:
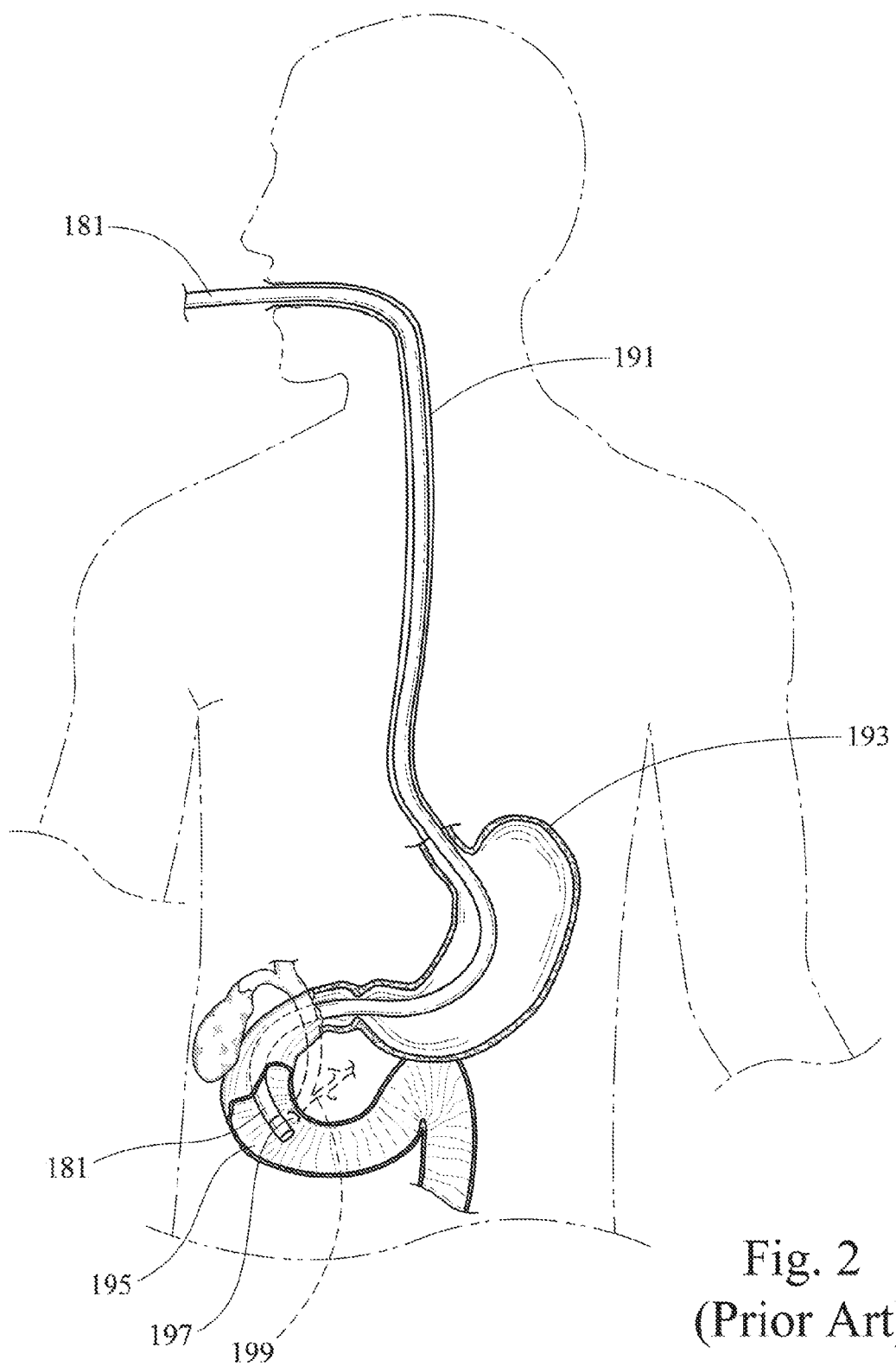
FIG. 2 shows an endoscope deployed in a patient body, indicating the sinuous, tortuous, and/or constricted path that a needle and stylet may need to follow (e.g., to access the head of a patient pancreas)

With prior devices, the stylet removal force can be quite high when a needle or other device through which the stylet is disposed is positioned through an endoscope contorted through a tortuous passage (e.g., as shown in FIG. 2). The natural/default disposition of the stylet wire is to straighten. Therefore when the stylet is being pulled around/through the bends of the needle, the stylet is continuously "trying" to straighten. This means that the distal tip of the stylet is continuously being scraped against the wall of the needle, increasing the interference and frictional force resisting retraction/removal. If the tip of the stylet is more malleable (in martensite state) is will conform the to shape of the needle upon removal. This effect will be seen more in larger-gauge needles that contain correspondingly larger stylets. The same would apply for stylet embodiments with a polymeric tip, where the polymeric tip will be constructed of a material that is softer/less stiff than the wire employed for the major body length of the polymer-tipped stylet embodiments.

The distalmost end length 504 of the single-wire body 502 is shown with enlarged portions 504a that may help secure the polymeric distal tip member 506 along with other fastening means (such as, for example, epoxy, adhesive, etc.) although, as above, the enlarged portion may function alone to secure these elements together. The enlarged portion 504a is shown as having a barbed geometry, but those of skill in the art will appreciate that other shapes can be provided to assist inter-engagement of the distalmost end length 504 with the polymeric distal tip member 506. The distalmost end length 504 of the single-wire body 502 preferably occupies one-half or less of the longitudinal length of the polymeric distal tip member 506. As such, the unoccupied distal-most length of the polymeric distal tip member 506 preferably will be even more flexible than the martensitic phase contacting/immediately-adjacent length of the single-wire body 502, which will further provide for decreasing likelihood of binding/increased retraction force attributable to stylet stiffness through certain lengths of a needle lumen (or other lumen) during use.

Figure 4C:
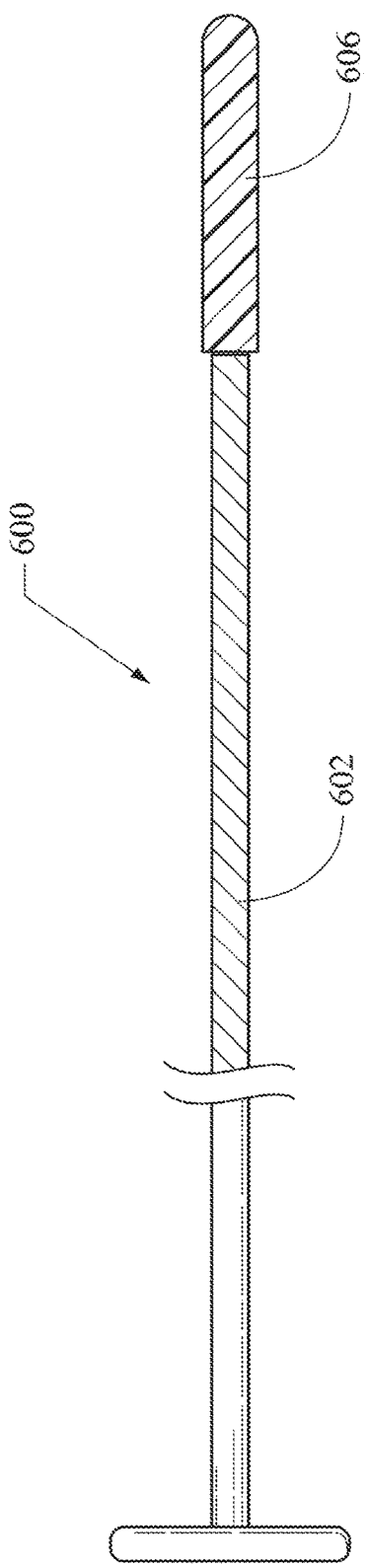

Yet another embodiment of a stylet for use within an endoscopy needle is described with reference to FIG. 4C, which shows a simplified/diagrammatic longitudinal section view of a sixth stylet embodiment 600. The stylet 600 includes an elongate single-wire, memory-metal alloy body 602 with a generally cylindrical body profile that is circumferentially bounded by a first outer circumference. A polymeric distal tip member 606 is fixedly attached directly at a distal end of the single-wire body 602. The polymeric distal tip member 606 has a generally cylindrical body profile like the single-wire body 602, and it is circumferentially bounded by a second outer circumference that is greater than the first outer circumference, while including a hemispherically-rounded or otherwise domed distal end terminus.

Each of the above embodiments may be useful in methods for accessing a target site via a tortuous passage. For example, a tortuous passage may include patient body passage and/or an endoscope, introducer sheath, or other passage where a more-flexible distalmost portion will be advantageous for navigating a needle (with stylet in its lumen) and retracting the stylet with less force than required for a stylet having consistent flexibility along its entire length. The target site may be within a patient's body. The stylet may include memory metal material and/or polymeric length(s) as described above, alone or in combination with each other.

Those of skill in the art will appreciate that embodiments not expressly illustrated herein may be practiced within the scope of the claims, including that features described herein for different embodiments may be combined with each other and/or with currently-known or future-developed technologies while remaining within the scope of the claims. Although specific terms are employed herein, they are used in a generic and descriptive sense only and not for purposes of limitation unless specifically defined by context, usage, or other explicit designation. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved equally with every embodiment. In the event of any inconsistent disclosure or definition from the present application conflicting with any document incorporated by reference, the disclosure or definition herein shall be deemed to prevail.

We claim:

1. A stylet configured for use within an endoscopic needle, the stylet comprising:
    a proximal end terminus and a distal end terminus;
    an elongate single-wire, memory-metal alloy body with a generally cylindrical body profile that is circumferentially bounded by a first outer circumference, extending distally from the proximal end terminus;
    a polymeric distal tip member fixedly attached directly at a distal end of the single-wire body;
    where the polymeric distal tip member has a generally cylindrical body profile circumferentially bounded by a second outer circumference that is substantially equal to or greater than the first outer circumference;
    where at least a lengthwise portion of the single-wire body is in martensitic phase at operating temperatures at and below about 37° C.,
    where the polymeric distal tip member is overmolded upon and around a distal terminal-end length of the single-wire body, and
    where the longitudinal distal terminal-end length of the single-wire body that is within the polymeric distal tip member occupies about one-half or less of the longitudinal length of the polymeric distal tip member.

2. The stylet of claim 1, where the fixed attachment of the polymeric distal tip member to the single-wire body comprises one or more of overmolding, adhesive, epoxy, friction-fit interface, or any combination thereof.

3. The stylet of claim 1, where a combined length of
    the polymeric distal tip member
    and
    the lengthwise portion of the single-wire body in martensitic phase at operating temperatures at and below about 37° C.
    comprises at least about one-tenth of a complete length of the stylet between its proximal end terminus and distal end terminus.

4. The stylet of claim 1, where a combined length of
    the polymeric distal tip member
    and
    the lengthwise portion of the single-wire body in martensitic phase at operating temperatures at and below about 37° C.
    comprises no more than about one-half of the complete length of the stylet between its proximal end terminus and distal end terminus.

5. The stylet of claim 1, where a length of the polymeric distal tip member comprises
    at least about one-half of a complete length of the stylet between its proximal end terminus and distal end terminus, or
    no more than about one-half of a complete length of the stylet between its proximal end terminus and distal end terminus.

6. The stylet of claim 1, where the distal terminus of the polymeric distal tip member is hemispherical or otherwise rounded.

7. A needle assembly including the stylet of claim 1, further comprising an endoscopic needle, where the stylet is disposed through a longitudinal lumen of the endoscopic needle.

8. A stylet configured for use within an endoscopic needle, the stylet comprising:

a proximal end terminus and a distal end terminus;

an elongate single-wire, memory-metal alloy body with a generally cylindrical body profile that is circumferentially bounded by a first outer circumference, extending distally from the proximal end terminus;

a polymeric distal tip member fixedly attached directly at a distal end of the single-wire body;

where the polymeric distal tip member has a generally cylindrical body profile circumferentially bounded by a second outer circumference that is substantially equal to or greater than the first outer circumference; and where at least a lengthwise portion of the single-wire body is in martensitic phase at operating temperatures at and below about 37° C., where the polymeric distal tip member is overmolded upon and around a distal terminal-end length of the single-wire body, where the second outer circumference is substantially equal to the first outer circumference, and the longitudinal distal terminal-end length of the single-wire body that is within the polymeric distal tip member comprises a third outer circumference that is less than the first outer circumference and the second outer circumference, and where the longitudinal distal terminal-end length of the single-wire body that is within the polymeric distal tip member occupies about one-half or less of the longitudinal distal terminal-end length of the polymeric distal tip member.

9. The stylet of claim 8, where the third outer circumference is about 65% to about 95% of the second outer circumference.

10. The stylet of claim 8, where the second outer circumference is greater than the first outer circumference.

11. The stylet of claim 8, where the first outer circumference is about 65% to about 95% of the second outer circumference.

12. The stylet of claim 8, where a combined length of the polymeric distal tip member and the lengthwise portion of the single-wire body in martensitic phase at operating temperatures at and below about 37° C.

comprises no more than about one-half of the complete length of the stylet between its proximal end terminus and distal end terminus.

13. The stylet of claim 8, where a length of the polymeric distal tip member comprises at least about one-half of a complete length of the stylet between its proximal end terminus and distal end terminus, or no more than about one-half of a complete length of the stylet between its proximal end terminus and distal end terminus.

14. The stylet of claim 8, where the distal terminus of the polymeric distal tip member is hemispherical or otherwise rounded.

15. A needle assembly including the stylet of claim 8, further comprising an endoscopic needle, where the stylet is disposed through a longitudinal lumen of the endoscopic needle.

16. The stylet of claim 8, where a combined length of the polymeric distal tip member and the lengthwise portion of the single-wire body in martensitic phase at operating temperatures at and below about 37° C.

comprises at least about one-tenth of a complete length of the stylet between its proximal end terminus and distal end terminus.

* * * * *